United States Patent [19]

Hatch

[11] 4,187,183

[45] Feb. 5, 1980

[54] MIXED-FORM POLYHALIDE RESINS FOR DISINFECTING WATER

[75] Inventor: Gary L. Hatch, Milwaukee, Wis.

[73] Assignee: Aqua-Chem, Inc., Milwaukee, Wis.

[21] Appl. No.: 920,260

[22] Filed: Jun. 29, 1978

Related U.S. Application Data

[63] Continuation of Ser. No. 656,416, Feb. 9, 1976, abandoned, which is a continuation of Ser. No. 563,068, Mar. 28, 1975, abandoned.

[51] Int. Cl.$^2$ ............................................. C02B 3/06
[52] U.S. Cl. .................................... 210/501; 210/29; 210/62; 210/64; 422/37; 424/79; 424/150
[58] Field of Search ................. 210/29, 62, 64, 501, 210/37 R; 422/30, 37; 424/79, 150; 521/30

[56] References Cited

U.S. PATENT DOCUMENTS

| | | | |
|---|---|---|---|
| 3,136,716 | 6/1964 | Kitter | 210/62 |
| 3,161,588 | 12/1964 | Zsoldos | 210/64 |
| 3,346,446 | 10/1967 | Zsoldos | 210/62 |
| 3,425,790 | 2/1969 | Sloan | 210/62 |
| 3,462,363 | 8/1969 | Mills | 210/62 |
| 3,817,860 | 6/1974 | Lambert et al. | 210/64 |
| 3,872,013 | 3/1975 | Nishino et al. | 210/501 |

*Primary Examiner*—Thomas G. Wyse

[57] ABSTRACT

A strongly basic anion-exchange resin loaded with iodine and a less than stoichiometric amount of an iodide salt or bromine and a less than stoichiometric amount of bromide salt is an effective demand bactericide for disinfecting water. The bactericidal resin according to the invention elutes only small amounts of halide ions and is especially suited for killing bacteria in feed water supplies having relatively high salt content.

3 Claims, No Drawings

MIXED-FORM POLYHALIDE RESINS FOR DISINFECTING WATER

This is a continuation of application Ser. No. 656,416, filed on Feb. 9, 1976, abandoned which in turn was a continuation in part of application Ser. No. 563,068, filed Mar. 28, 1975, abandoned.

BACKGROUND OF THE INVENTION

The present invention relates generally to the art of water disinfecting, and in particular to a novel bactericidal mixed-form polyhalide resin. This is a continuation in part of Ser. No. 563,068 filed Mar. 28, 1975.

Several techniques are known for killing bacteria in water. One such method includes treating the water with halogens, but because this method leaves large residual concentrations of halogens in the treated water, its usefulness has been limited to the treatment of swimming pools and the like. Another method involves the use of polyhalide resin bactericides of one single form or another. For example, bromine can be eluted from a strong base anion-exchange resin at concentrations ranging from 10 to 10,000 p.p.m. Residual bromine is captured by a scavenger resin to reduce the final bromine level to 1.0 p.p.m. or below. Another water disinfecting technique involves the use of an anion-exchange resin fully loaded with triiodide ($I_3^-$) ions.

The latter technique, while being useful for a wide variety of different feed waters, has one drawback when the feed solution contains relatively high salt concentrations, i.e., 250 p.p.m. as sodium chloride or greater. While little free iodine is eluted from the resins, relatively large quantities of iodide ions are eluted. A resin which elutes reduced levels of iodide ions under these conditions would be a significant improvement in this water treatment technology.

OBJECTS OF THE INVENTION

It is a primary object of the present invention to provide a novel bactericidal and virucidal mixed-form polyhalide resin.

Another object of the present invention is to provide such a resin which is useful for treating feed solutions containing relatively high salt concentrations.

A further object of the present invention is to provide such a resin which elutes reduced levels of halide ions when used to treat feed solutions having relatively high salt concentrations.

How these and other objects of the present invention are achieved will be described in the following specification. Generally, however, the invention comprises a mixed-form polyhalide bactericidal and virucidal resin prepared by adding to a strong base anion-exchange resin a slurry mixture of elemental iodine, interhalogen, or bromine and an appropriate amount of an iodide or bromide salt. The preferred amount of iodide or bromide is less than the stoichiometric amount required for complete loading of triiodide or tribromide ions on all available resin sites and the $X_2:X^-$ ratio is always greater than one. Iodine or bromine liberated from such bactericidal resins during water treatment may be readily scavenged by an unloaded anion-exchange resin and the hypohalous acid can be removed by further treatment with activated charcoal.

DESCRIPTION OF THE PREFERRED EMBODIMENT

In accordance with one preferred form of the present invention a stong base anion-exchange resin, preferably in chloride form, is reacted with a mixture of iodine and a pre-selected amount of iodide salt to form a mixed-form polyhalide resin product. For purposes of the following description, iodine and an iodide salt will be discussed, but bromine or an appropriate interhalogen may be substituted for iodine, and a bromide salt may be substituted for the iodide salt to produce other mixed-form resins within the scope of the present invention.

A number of commercially available strong base anion-exchange resins are useful as the starting material for preparation of the resin of the present invention, including those containing strongly basic (cationic) groups such as quaternary ammonium groups, tertiary sulfonium groups, quaternary phosphonium groups or alkyl pyridinium groups. Expecially preferred are the quaternary ammonium resins such as Rexyn 201 (Fisher Scientific Co.), Amberlite IR A-400 and Amberlite IR A-401S (Mallinckrodt Chemical Works), Ionac A-540 (Matheson, Coleman and Bell), Dowex I and Dowex 21K (Dow Chemical Co.); and Duolite A-101D and ES-109 (Diamond Shamrock Chemical Co.). The resins are usually supplied in the chloride form as granuals or beads of various mesh sizes.

The resin chosen for use in the present invention is measured on a wet volume basis to determine its ionic loading capacity and is transferred to a suitable container with a minimum volume of water. In a separate container, a preselected amount of crystalline iodine is mixed with a preselected amount of potassium or other water soluble iodide salt, and just enough water to dissolve the reactants. The amounts of iodine and potassium iodide is selected according to either Table I or Table II, which will be discussed below. The iodine and iodide salt are mixed until the ingredients are completely dissolved. The resultant mixture consists of triiodide ($I_3^-$) ions and the superpolyiodide, $I_5^-$. The resulting mixture is added to the anion-exchange resin in chloride form and mixed therewith for a time sufficient to permit complete absorption of the iodine and iodide ions on the exchange sites of the resin, for example 24–72 hours.

TABLE I

| R : $I_2$ : KI Ratio | % A ($I_3^-$)* | % B ($I_5^-$)* |
|---|---|---|
| 1 1.2 1 | 80% | 20% |
| 1 1.1 1 | 90% | 10% |
| 1 1.0 .9 | 80% | 10% |
| 1 1.0 .8 | 60% | 20% |
| 1 1.0 .7 | 40% | 30% |

*anion forms shown are believed to be predominant species when A, B, Y and Z = I for which n=1 and m=2.

The data contained in Table I was derived from basic stability data for the iodide anions. A similar table could be prepared for the bromide or interhalogen anions using appropriate stability data.

The anions of the mixed-form polyhalide resin have the general formula $-a(A_{2n}Y)^- + b(B_{2m}Z)^-$, wherein:

$0 < (a \text{ and } b) < 1$;

$a + b \leq$ total resin sites available for exchange;

A and B = I or Br;

Y and Z = Cl, Br or I;

if A = B and Y = Z, then m cannot equal n;

n and m are whole numbers in excess of 0.

As seen in Table I, the stoichiometric ratio of $I_2$:KI is always greater than 1, so that the resultant bactericidal resin is of mixed form. The actual value of a and b depends on not only the resin: $X_2$:KX ratio but also on the relative stabilities of resin $+-(A_{2n}Y)^-$ and resin $+-(B_{2m}Z)^-$. For instance, in Table I for resin: $I_2$:KI = 1.0:1.0:0.8 the values for a and b are believed to be approximately 0.6 and 0.2, respectively. This belief is based on experimental evidence which indicates that the stability of $[Resin^{\oplus}-(I_3^{\ominus})] > [Resin^{\oplus}-(I_5^{\ominus})] >> [Resin^{\oplus}-(I_2Cl^{\ominus})]$, the latter resulting from reaction of $I_2$ with the original chloride form resin. As can be visualized, then, the resin can consist of three or more species of polyhalide anions. However, the satisfaction of stability requirements usuallu leads to the formation of two predominant species of which the resin is expected to be comprised and which results in the formation of only small equilibrium amounts of other polyhalide anions.

TABLE II

Effect of Resin:$I_2$:KI Equivalent Ratio on Iodine Release - 100 ml Mixed-Form Resin Bed; 160 ml/min. Flow Rate.

| Resin: $I_2$: KI Ratio | PPM $I_2$ Released* | | PPM $I^-$ Exchanged | |
|---|---|---|---|---|
| | In- itially | After 34 Bed Volumes of 2M NaCl Wash | In- itially | After 34 Bed Volumes of 2M NaCl Wash |
| 1.0:1.2:1.0 | 1.97 | — | 0.80 | — |
| 1.0;1.1:1.0 | 0.79 | — | 0.68 | — |
| 1.0:1.0:0.9 | 0.82 | 0.99 | 3.78 | .5 |
| 1.0:1.0:0.8 | 1.23 | 1.34 | 1.90 | .27 |
| 1.0:1.0:0.7 | 1.42 | 1.56 | 0.21 | 0.0 |

*The release of $I_2$ and exchange of $I^-$ may vary slightly depending on the base resin employed and may even vary for the same resin from batch to batch. For example other measurements on different batches of one mixed-form resin having a resin-:$I_2$:KI ratio of 1.0:1.0:.8 yielded $I_2$ elution quantities of from 1.45–2.08 ppm and $I^-$ exchange of from .55–.66 ppm.

It can be seen from Table II that the quantity of elemental iodine and iodide ions eluted from the resin of the present invention varies significantly depending on the Resin:$I_2$:KI stoichiometric ratio. Table II was prepared using a 412 p.p.m. salt (NaCl) solution as the feed liquid to simulate extreme feed water conditions. One preferred Resin:$I_2$:KI Ratio is 1.0:1.0:0.8 because the resin product elutes only approximately 1.34 p.p.m. elemental iodine.

Table II shows that the properties of the resins prepared according to the method described above may be further modified by washing with 34 bed volumes (approximately one gallon) of 2 M sodium chloride solution. It is believed that the additional washings with concentrated salt solution remove exchangeable iodide ions from the resins, replacing then with chloride ions from the salt solution. This in effect decreases the $I^-$:Resin ratio which then allows an increase in the elution of elemental iodine.

Throughout the discussion of the present invention, reference has been made to decreasing the halide elution, even though, as shown in Table II, the halogen concentration is increased. The latter is permissible because the halogen released from the resins can be readily removed by a scavenger resin, the preferred ones of which are unloaded strong base anion-exchange resins as described above. These resins are much more efficient in removing halogens than the corresponding halide ions. Scavenger efficiency is maximized in those cases where the eluted concentration of $I_2 \geq I^-$, which as shown by Table II is the case for the mixed-form resins of the present invention. The scavenger resins may be used in tandem with the treating resin to yield treated water which has halide and halogen concentrations each substantially below 1.0 p.p.m. Of course, the scavenger resin need not be used if the end use of the treated water has halogen tolerance limits exceeding the halogen concentrations shown in Table II.

The bactericidal efficiency of the resin with a Resin-:$I_2$:KI ratio of 1.0:1.0:0.8 is shown in Table III.

TABLE III

Bactericidal Efficiency of Resin with Resin:$I_2$:KI Ratio of 1.0:1.0:0.8

| Test | Resin Volume (ml) | | Flow Rate B.V./min. | E. Coli | |
|---|---|---|---|---|---|
| | Mix-form Resin | Scavenger | | Inoculum | Effluent* |
| 1 | 100 | — | 1.0 | 3.0×10 5/ml | 1/100 ml |
| 2 | 150 | 75 | 1.3 | 3.0×10 5/ml | 1/100 ml |
| 3 | 100 | — | 1.6 | 3.5×10 5/ml | 1/100 ml |
| 4 | 100 | — | 1.6 | 1.5×10 6/ml | 1/100 ml |
| 5 | 50 | — | 3.7 | 1.8×10 5/ml | 1/100 ml |
| 6 | 50 | — | 3.7 | 3.3×10 5/ml | 1/100 ml |

All effluents were negative for coliform bacteria as indicated by both the plate count and Fermentation Tube Test Methods.

Further research into the treatment of water according to the present invention has led to the discovery that when using the mixed-form resins having a KI:Resin ratio of less than one, especially with low salt feed solutions, a significant and possibly desirable amount of hypoiodous acid (HOI) is produced in the treatment system (Table IV).

TABLE IV

Hypoiodous Acid (HOI) Production from Resin with Resin:$I_2$:KI Ratio of 1.0:1.0:0.8

| Treatment System | | | | | Effluent Analysis | |
|---|---|---|---|---|---|---|
| Mixed-form Resin (ml) | Scavenger Resin (ml) | Charcoal (ml) | Influent Water | Flow Rate B.V./min. | PPM HOI (as $I^+$) | PPM $I_2$ |
| 150 | — | — | Deionized water | 1.33 | 1.8 | 1.0 |
| 150 | — | — | Deionized water | 4.67 | 2.2 | 1.4 |
| 150 | 75 | — | Deionized water | 4.67 | 1.6 | 0 |
| 200 | 260 | — | 250 ppm NaCl | 4.0 | 0.22 | 0 |

TABLE IV-continued
Hypoiodous Acid (HOI) Production from Resin with Resin:I₂:KI Ratio of 1.0:1.0:0.8

| Treatment System | | | | | Effluent Analysis | |
|---|---|---|---|---|---|---|
| Mixed-form Resin (ml) | Scavenger Resin (ml) | Charcoal (ml) | Influent Water | Flow Rate B.V./min. | PPM HOI (as I⁺) | PPM I₂ |
| 200 | 260 | 60 | 250 ppm NaCl | 4.0 | 0.12 | 0 |

The proposed reaction scheme offers an explanation of the hypoiodous acid production:

$$Resin^{\oplus} - I_5^{\ominus} \rightarrow Resin^{\oplus} - I_3^{\ominus} + I_2; \quad (1)$$

$$I_2 + H_2O \rightleftharpoons H^+ + I^- + HOI; \quad (2)$$

$$I_2 + I^- \rightleftharpoons I_3^-; \quad (3)$$

$$Resin^{\oplus} - Cl^{\ominus} + I_3^- \rightarrow Resin^{\oplus} - I_3^{\ominus} + Cl^-; \quad (4)$$

the net result being the formation of $2[Resin^{\oplus} - I_3^{\ominus}] + H^+ + Cl^- + HOI$.

With $Resin^{\oplus} - Cl^{\ominus}$ having a high affinity for $I_3^-$, reaction (3) is shifted far to the right. With excess $I_2$ produced by reaction (1), and with reaction (3) consuming $I^-$, reaction (2) is shifted far to the right which results in excessive production of hypoiodous acid.

The hypoiodous acid is an effective virus killer, approximately four times more effective than molecular iodine itself, but if the final use of the treated water precludes even small concentrations of such acid, a substantial percentage of it may be effectively removed by employing activated charcoal as a third stage in the water treatment system.

The resins according to the present invention may be employed not only for such large scale jobs such as sterilizing water for swimming pools, but may also be used in either industrial or residential devices for purifying water for human consumption. The invention solves a problem apparently not recognized in the prior art, i.e., the reduction of undesirable halide concentrations. While one particular Resin:X₂:KX Ratio has been disclosed as preferred, the amount of halide salt and halogen used in such method can be selected by one skilled in the art depending on the particular end use of the treated water. So while the invention has been described in connection with a particular preferred embodiments, the invention is not to be limited thereby, but is to be limited solely by the claims which follow.

I claim:

1. A mixed-form polyhalide bactericidal resin comprising a strong base anion-exchange resin having anion exchange sites and having attached to a predominant number of such sites polyhalide anions of the following formulas:

$$a(I_3^-) \text{ and } b(I_5^-);$$

wherein:
- $a = 0.4$ to $0.8$ of the exchange sites;
- $b = 0.1-0.3$ of the exchange sites;
- $a + b =$ a predominant number of the anion sites available for exchange; and
- $a + 2(b)$ equals or exceeds 1.0.

2. The resin as claimed in claim 1 wherein $a = 0.6$ and $b = 0.2$.

3. The resin as claimed in claim 1 wherein said resin is a quanternary ammonium anion-exchange resin.

* * * * *